US00PP21937P2

(12) United States Plant Patent
Bradford

(10) Patent No.: US PP21,937 P2
(45) Date of Patent: May 31, 2011

(54) INTERSPECIFIC TREE NAMED 'SWEETCOT II'

(50) Latin Name: ***Prunus* sp.**
Varietal Denomination: Sweetcot II

(76) Inventor: Lowell Glen Bradford, Le Grand, CA (US)

( * ) Notice: Subject to any disclaimer, the term of this patent is extended or adjusted under 35 U.S.C. 154(b) by 0 days.

(21) Appl. No.: 12/655,118

(22) Filed: Dec. 24, 2009

(51) Int. Cl.
*A01H 5/00* (2006.01)

(52) U.S. Cl. ..... Plt./180

(58) Field of Classification Search ..... Plt./180
See application file for complete search history.

(56) References Cited

U.S. PATENT DOCUMENTS

| | | | |
|---|---|---|---|
| PP2,539 | P | 6/1965 | Anderson |
| PP7,431 | P | 1/1991 | Bradford |
| PP15,652 | P2 | 3/2005 | Bradford |

*Primary Examiner* — Susan B McCormick Ewoldt

(57) ABSTRACT

The present invention relates to an interspecific tree and more particularly to a new and distinct variety broadly characterized by a medium size, moderately vigorous, and hardy tree with apricot type leaves. Being self-unfruitful, the present variety requires cross pollinization from an apricot that blooms during the early season, such as 'Castlebrite' (unpatented). The present variety is pollen deficient and does not attract bees, so the pollinator must be placed in very close proximity. The fruit matures under the ecological conditions described during the last week in May, with first picking on May 24, 2009. The fruit is medium in size, full red in skin color, freestone in type, orange yellow in flesh color, firm in texture, sweet in flavor, and has skin pubescence.

1 Drawing Sheet

Botanical classification: *Prunus* sp.
Variety denomination: 'SWEETCOT II'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits. The present invention relates to a new and distinct variety of interspecific tree, which has been denominated varietally as 'SWEETCOT II'.

During the 1998 blooming season I isolated an entire 'Red Beaut' (U.S. Plant Pat. No. 2,539) plum tree by covering it with a plastic house. I placed a hive of bees inside the house and brought various bouquets from different apricot trees to hybridize the 'Red Beaut' plum tree. Upon the completion of the bloom, the house and bees were removed and the resulting fruit was allowed to ripen. Upon maturity, the fruit was harvested and their seeds were germinated and grown as seedlings on their own root in my greenhouse. Upon reaching dormancy that fall, the seedlings were transplanted to a cultivated area of my experimental orchard near Le Grand, Calif. in Merced County (San Joaquin Valley). The group of seedlings was labeled "House 10". During the 2002 evaluation season, I selected the present variety as a single tree from the group of seedlings described above. The present variety exhibited several indications that it was itself an interspecific, such as fruit with pubescent skin and orange yellow flesh. Subsequent to origination of the present interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Red Beaut' (U.S. Plant Pat. No. 2,539) plum, by being self-unfruitful and by producing fruit that is globose in shape, firm in texture, full red in skin color, and matures in late May, but is very distinguished therefrom by having apricot type leaves and by producing fruit that has pubescent skin, that is orange yellow in flesh color, and that is much sweeter in flavor.

The present variety is similar to 'Sweetcot' (U.S. Plant Pat. No. 15,652) interspecific tree by being self-unfruitful, by having apricot type leaves and blossoms, by producing very little pollen and by producing fruit that is globose in shape, orange yellow in flesh color, firm in texture, pubescent in skin surface, and quite juicy, but is distinguished therefrom by producing fruit that is red in skin color instead of dark purple and that matures about thirty days earlier.

The present variety is most similar to 'Royal Velvet' (U.S. Plant Pat. No. 7,431) Plum-apricot hybrid tree by being self-unfruitful, by having apricot type leaves, by producing very little pollen, and by producing fruit that ripens in the early season and that is globose in shape, orange yellow in flesh color, full red in skin color, pubescent in skin surface, and quite juicy, but is distinguished therefrom by producing fruit that is larger in size, firmer in texture, freestone instead of clingstone, and that has a bitter tasting kernel instead of sweet.

SUMMARY OF VARIETY

The present interspecific variety is characterized by a medium size, moderately vigorous, and hardy tree with apricot type leaves. Being self-unfruitful, the present variety requires cross pollinization from an apricot that blooms during the early season, such as 'Castlebrite' (unpatented). The present variety is pollen deficient and does not attract bees, so the pollinator must be placed in very close proximity. The fruit matures under the ecological conditions described during the last week in May, with first picking on May 24, 2009. The fruit is medium in size, full red in skin color, freestone in type, orange yellow in flesh color, firm in texture, sweet in flavor, and has skin pubescence.

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif., and was developed at the state of shipping ripe on May 27, 2009, on a multiplied tree using Nemaguard rootstock during its ninth growing season. All major color code designations are by reference to The Inter-Society Color Council, National Bureau of Standards. Common color names are also used occasionally.

Tree

Size: Medium, reaching and maintaining a height of 9' [2.74 m.] and a spread of 11' [3.35 m.] after nine growing seasons utilizing typical dormant pruning.

Vigor: Moderately vigorous, responding typically to irrigation and fertilization. The variety grows about 2' [0.6 m.] of surplus top-growth during the spring and summer. The tree should be grown on a commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Medium productivity if pollinated sufficiently during the blooming season.

Fertility: Self-unfruitful, requiring cross pollination by a suitable early seasonal blooming apricot, such as 'Castlebrite' (unpatented).

Bearing: Uncertain bearer, very dependent upon the weather during the blooming season.

Trunk:

- *Size.*—Medium, reaching a maximum diameter of 5" [127 mm.] after the ninth growing season.
- *Texture.*—Medium shaggy.
- *Bark color.*—A Dark grayish yellowish brown [81. d.gy.yBr] and Deep brown [56. deep Br] variegation.
- *Lenticels.*—Approximate Number Per Square Inch: 10. Color: Strong yellowish brown [74. s.yBr]. Typical Size: 5/16" [8.0 mm.].

Branches:

- *Size.*—Diameter of limb is 2½" [63.5 mm.] measured 12" above the crotch, 1½" [38.1 mm.] measured 12" above the secondary fork.
- *Texture.*—Smooth on first year wood, rough on second year wood, and shaggy on third year and older wood.
- *Color.*—1st Year Wood Topside: Light reddish brown [42. l.rBr]. 1st Year Wood Underside: Strong yellow green [117. s.YG]. Second Year Wood: Strong brown [55. s.Br].
- *Lenticels.*—Approximate Number Per Square Inch: 120 on second year wood. Color: Light grayish yellowish brown [79. l.gy.yBr]. Typical size: 1/64" [0.4 mm.].

Leaves:

- *Size.*—Medium. Average Length: 3½" [89 mm.]. Average width: 2" [51 mm.].
- *Arrangement.*—Alternate.
- *Thickness.*—Medium.
- *Form.*—Oval.
- *Apex.*—Acuminate.
- *Base.*—Obtuse with a base angle of 110 degrees.
- *Surface.*—Smooth.
- *Color.*—Dorsal Surface: Moderate olive green [125. m.OlG]. Ventral Surface: Strong yellow green [117. s.YG].
- *Margin.*—Finely serrate.
- *Venation.*—Pinnately net veined.
- *Vein color.*—Brilliant yellow green [116. brill.YG].
- *Petiole.*—Average Length: 15/16" [23.8 mm.]. Average Thickness: 3/64" [1.2 min.]. Color: Very yellow green [115. v.YG].
- *Stipules.*—Number: 2 per young leaf occurring only near the growing tip. Average Length: 5/16" [7.9 mm.]. Color: Grayish reddish orange [39. gy.rO].
- *Glands.*—Number: 2 or less per leaf. Position: Alternate. Size: Small. Form: Globose. Color: Moderate yellow green [120. m.YG] becoming Light reddish brown [42. l.rBr] with age.
- *Leaf Buds.*—Medium, pointed.

Flower buds:

- *Hardiness.*—Hardy, with respect to central California winters.
- *Diameter.*—Typically 3/16" [4.8 mm.] 3 days before bloom.
- *Length.*—Typically 3/8" [9.5 mm.] 3 days before bloom.
- *Form.*—Not appressed.
- *Surface.*—Pubescent.
- *Color.*—White [263. White] at the tip.

Flowers: Perfect, complete, perigynous, usually a single pistil, about twenty-four stamens, five sepals and petal locations alternately positioned.

- *Average flower diameter.*—13/16" [20.7 mm.].
- *Number of petals.*—Usually five.
- *Petal shape.*—Circular.
- *Petal margin.*—Slightly wavy.
- *Average petal diameter.*—3/8" [9.5 mm.].
- *Average petal length.*—3/8" [9.5 mm.].
- *Petal apex.*—Rounded.
- *Petal base.*—Rounded.
- *Petal color.*—White [263. White].
- *Anther color.*—Pale yellowish pink [31. p.yPk].
- *Stigma color.*—Light greenish yellow [101. l.gY].
- *Sepal color.*—A Deep purplish red [256. deep pR] and Moderate greenish yellow [102. m.gY] two-tone.
- *Sepal length.*—5/32" [4.0 mm.].
- *Sepal width.*—1/8" [3.2 mm.].
- *Average pistil length.*—9/16" [14.3 mm.].
- *Average stamen length.*—7/16" [11.1 mm.].
- *Fragrance.*—Moderate.
- *Pollen production.*—Slight to none.

*Blooming period.*—Early compared to apricots and plums, with Castlebrite (unpatented) apricot.
*Onset of bloom.*—One percent on Feb. 12, 2009.
*Date of full bloom.*—Feb. 21, 2009.
*Duration of bloom.*—One to two weeks, dependent on ambient temperature.
*Number per cluster.*—Average 5, up to 10 observed.

FRUIT

Maturity when described: Shipping ripe, May 27, 2009.
Date of first picking: May 24, 2009.
Date of last picking: Jun. 2, 2009.
Size: Uniform, medium compared to apricots.
*Average diameter axially.*—2 3/16" [53 mm.].
*Average diameter across suture plane.*—2 1/4" [57 mm.].
*Typical weight.*—3.9 ounces [110 grams].
Form: Uniform, globose.
*Longitudinal section form.*—Round.
*Transverse section through diameter.*—Round.
Suture: An inconspicuous line becoming a very shallow groove toward the apex.
Ventral surface: Rounded.
Lips: Slight to none.
Cavity: Flaring, circular with suture showing on one side only.
*Depth.*—7/16" [11.1 mm.].
*Breadth.*—1" [25.4 mm.].
Base: Rounded to slightly truncate.
Apex: Rounded.
Pistil point: An inconspicuous Brownish pink [33. brPk] dot.
Stem: Medium.
*Average length.*—3/8" [9.5 mm.].
*Average width.*—3/32" [2.4 mm.].
Skin:
*Thickness.*—Medium.
*Surface.*—Typical apricot pubescence.
*Tenacity.*—Tenacious to flesh.
*Astringency.*—Astringent.
*Tendency to crack.*—None observed.
*Color.*—Very deep red [14. v.deep Red] blending into a Moderate red [15. m.R] background with virtually no freckling.
*Surface bloom.*—Absent.
*Pubescence.*—Moderate, does not roll up when rubbed, similar to an apricot.
Flesh:
*Color.*—Brilliant orange yellow [67. brill.OY] throughout.
*Surface of pit cavity.*—Covered with Strong orange yellow [68. s.OY] fibers.
*Amygdalin.*—Moderate.
*Juice.*—Abundant, very rich.
*Texture.*—Medium firm, melting.
*Fibers.*—Abundant, fine, tender.
*Ripens.*—Somewhat earliest at apex.
*Flavor.*—A tasty blend of acid and sugar with apricot prominence, typically 17 brix.
*Aroma.*—Slight.
*Eating quality.*—Very good.

STONE

Type: Freestone.
Form: Oval.
Hilum: Narrow, oblong.
Base: Rounded, oblique.
Apex: Obtuse.
Sides: Equal.
Surface: Rough throughout, like an apricot.
External color of stone: Moderate orange yellow [71. m.OY].
Pit wall color when cracked: Light yellowish brown [76. l.yBr].
Cavity surface color: Moderate yellowish pink [29. m.yPk].
Average pit wall thickness: 1/16" [1.6 mm.]
Average width: 7/8" [22.2 mm.].
Average length: 1 1/8" [28.6 mm.].
Average breadth: 7/16" [11.1 mm.].
Tendency to split: None observed.
Kernel:
*Form.*—Oval.
*Skin color.*—Yellowish white [92. yWhite].
*Pellicle color.*—Grayish yellow [90. gy.Y].
*Vein color.*—Grayish yellow [90. gy.Y].
*Taste.*—Somewhat bitter.
*Viable.*—Yes.
*Average width.*—1/2" [12.7 mm.].
*Average length.*—11/16" [17.5 mm.].
*Amygdalin.*—Moderate.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to 'Royal Velvet' (U.S. Plant Pat. No. 7,431) Plum-apricot hybrid tree by being self-unfruitful, by having apricot type leaves, by producing very little pollen, and by producing fruit that ripens in the early season and that is globose in shape, orange yellow in flesh color, full red in skin color, pubescent in skin surface, and quite juicy, but is distinguished therefrom by producing fruit that is larger in size, firmer in texture, freestone instead of clingstone, and that has a bitter tasting kernel instead of sweet.

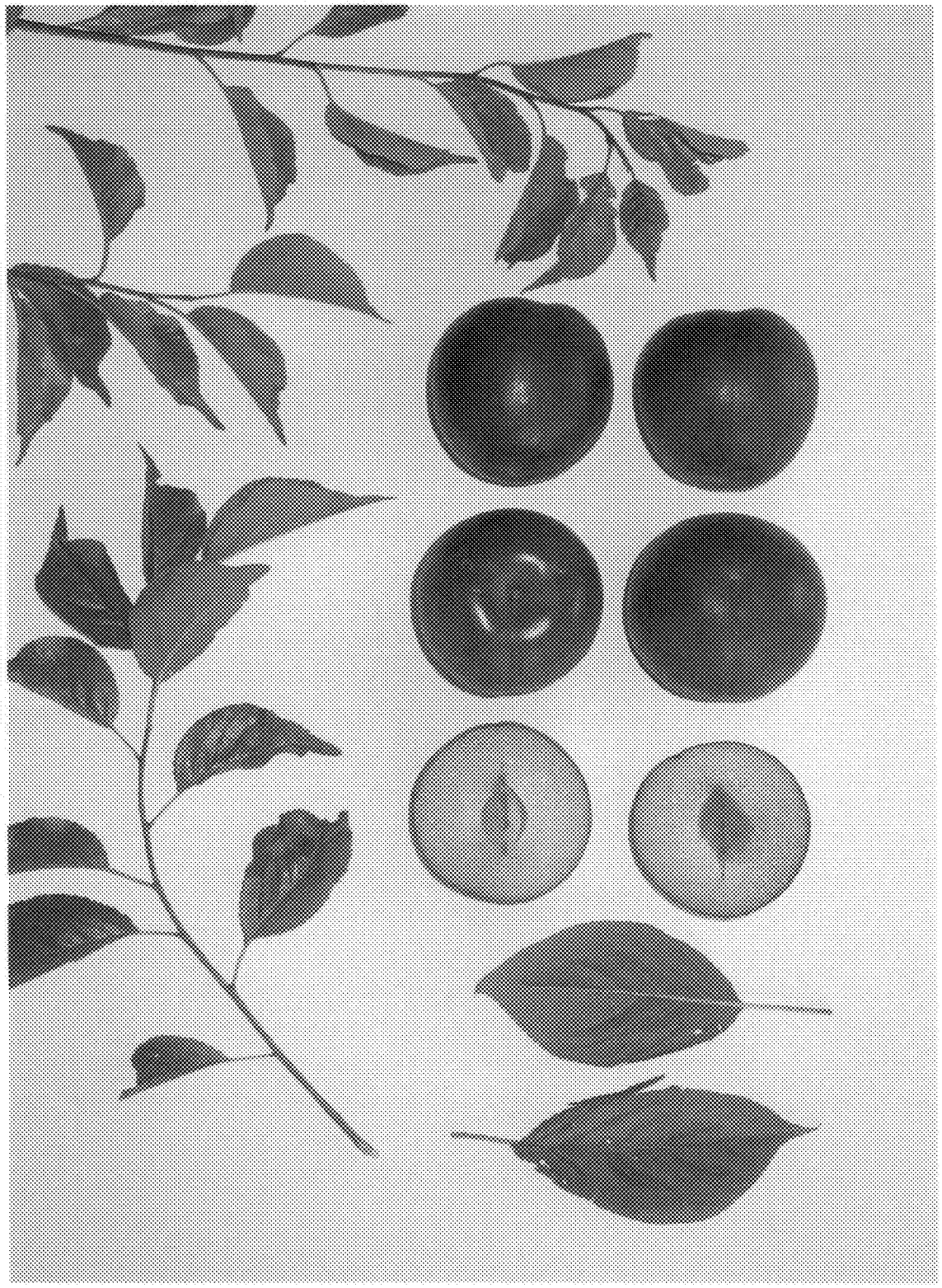

* * * * *